United States Patent
Braun et al.

(10) Patent No.: US 6,379,400 B1
(45) Date of Patent: Apr. 30, 2002

(54) DYE COMPOSITIONS AND METHODS OF DYEING KERATIN FIBERS

(75) Inventors: Hans-Juergen Braun, Ueberstorf; Pascal André Semadeni, Cordast, both of (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/581,367

(22) PCT Filed: Sep. 8, 1999

(86) PCT No.: PCT/EP99/06601

§ 371 Date: Jun. 12, 2000

§ 102(e) Date: Jun. 12, 2000

(87) PCT Pub. No.: WO00/21496

PCT Pub. Date: Apr. 20, 2000

(30) Foreign Application Priority Data

Oct. 13, 1998 (DE) .......................................... 198 47 192

(51) Int. Cl.$^7$ ................................................. A61K 7/13
(52) U.S. Cl. ............................................... 8/415; 8/423
(58) Field of Search ............................ 8/405, 414, 423, 8/565, 576, 577, 605

(56) References Cited

U.S. PATENT DOCUMENTS

| | | | | |
|---|---|---|---|---|
| 5,000,755 A | * | 3/1991 | Anderson ...................... | 8/405 |
| 5,078,749 A | * | 1/1992 | Anderson ...................... | 8/405 |
| 5,135,543 A | | 8/1992 | Chan et al. .................... | 8/405 |
| 5,387,295 A | * | 2/1995 | Gibson ...................... | 149/19.4 |
| 5,851,237 A | * | 12/1998 | Anderson et al. .............. | 8/409 |

FOREIGN PATENT DOCUMENTS

| | | | |
|---|---|---|---|
| CA | 900490 | * | 5/1972 |
| DE | 27 37 291 A | | 3/1978 |
| DE | 28 27 658 A | | 1/1979 |
| DE | 34 02 519 A1 | | 8/1985 |
| DE | 42 05 329 A | | 8/1993 |
| DE | 44 04 563 A | | 8/1995 |
| FR | 1 506 945 | | 3/1968 |
| FR | 1 584 965 A | | 1/1970 |
| FR | 2 211 210 A | | 7/1974 |

OTHER PUBLICATIONS

E. Sagarin : "Cosmetics, Science and Technology" (1957), interscience Publisher Inc., New York, pp. 503 FF.
H. Janistyn: "Handbuch Der Kosmetika Und Riechstoffe, Band 3", 1973, pp. 388–397.
ACS bib. of Yu et al, Huaxue Shiji, 15(1), pp. 35–36, 1993 (no month available).*
ACS bib. of Zorina et al, Dokl. Akad. Nauk SSSR, 308(5), pp. 1150–1154, 1989 (no month available).*
ACS bib. of Matsumura et al, Bull. Chem. Soc. Japan, 55(7), pp. 2174–2180, 1982 (no month available).*
ACS bib. of Minesinger et al, J. Phys. Chem., 78(5), pp. 494–497, 1974 (no month available).*
ACS bib. of Oberster et al., Can. J. Chem., 45(3), pp. 195–201, 1993 (no month available).*

* cited by examiner

*Primary Examiner*—Margaret Einsmann
(74) *Attorney, Agent, or Firm*—Michael J. Striker

(57) ABSTRACT

The dye composition has a pH of 3 to 12 and contains water, alcohols and/or mixtures thereof as a solvent; from 0.01 to 10 percent by weight of at least one dye compound of formula (I),

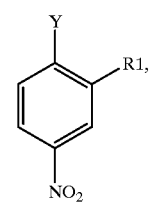

(I)

wherein R1 represents hydrogen or a methyl group and Y is an amino group of the formula —NHR2, and R2 is either a cyclopropyl group, a methoxyethyl group or a methoxypropyl group; OR wherein R1 represents hydrogen or a linear or branched alkyl group with 1 to 4 carbon atoms and Y represents a heterocyclic ring of formula (II):

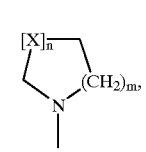

(II)

wherein X is a nitrogen atom or an oxygen atom and m is 1, 2 or 3 and n is 0 or 1; and from 0.5 to 30 percent by weight of at least one anionic, cationic, amphoteric and nonionic and/or zwitterionic surface-active substances and/or from 0.1 to 25 percent by weight of at least one thickener and/or from 0.1 to 5 percent by weight of at least one care material. A method of dyeing fibers using the composition is also described.

9 Claims, No Drawings

DYE COMPOSITIONS AND METHODS OF DYEING KERATIN FIBERS

BACKGROUND OF THE INVENTION

1. Field of the Invention

The present invention relates to compositions and methods for dyeing keratin fibers, especially human hair, and, more particularly, to compositions for dyeing keratin fibers, especially human hair, containing nitrophenylamines.

2. Prior Art

Nitro dyes have achieved a significant importance, especially for dyeing hair. In oxidizing hair dye compositions, they are an important constituent for modifying the dyeing result and for achieving fashionable color nuances. However, by combining yellow, red and blue nitro dyes, dyeing agents can also be produced, which are able to color hair in natural to fashionable shades without the addition of oxidizing agents.

Of particular importance in this connection are yellow nitro dyes, which are taken up directly and dye the hair an intensive lemon yellow, which is to be as free as possible from red portions. Furthermore, nitro dyes must also fulfill a whole series of additional requirements. For example, they must be safe from a toxicological and dermatological point of view and must make it possible to obtain dyed colors of the desired intensity. Among other things, this assumes that they are sufficiently soluble in water. In addition, a good light fastness, rubbing fastness, permanent waving fastness and perspiration resistance is required for the colorings achieved. On the other hand, the dyes should not wash out too easily once again during a subsequent treatment or when the hair is washed. Their use in oxidizing hair dye compositions presupposes furthermore that they are stable in the presence of reducing agents and oxidizing agents and especially in alkaline solution.

SUMMARY OF THE INVENTION

It is an object of the present invention to provide improved dye compositions containing nitrophenylamines, which meet the requirements for dyeing fibers, especially human hair, in an outstanding manner.

It is another object of the present invention to provide improved methods for dyeing keratin fibers, especially human hair, which utilizes the improved dye compositions.

Surprisingly, it has now been found that certain 4-nitrophenylamines have good water solubility and make an intensively luminous, yellow coloration possible. In addition, they have outstanding light fastness, rubbing fastness, permanent waving fastness and perspiration resistance.

The present invention therefore relates to compositions for dyeing fibers, particularly keratin fibers, such as human hair. The dye compositions are characterized in that they contain at least one compound of formula (I)

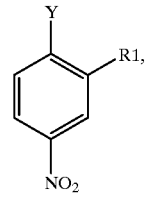

(I)

wherein, independently of one another
R1 represents hydrogen or a linear or branched alkyl group with 1 to 4 carbon atoms and
Y is a heterocyclic ring of formula (II)

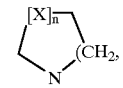

(II)

with X representing nitrogen or oxygen, m is 1, 2 or 3 and n is 0 or 1; or Y is an amino group $NR^2R^3$, and $R^2$ and $R^3$, independently of one another, each represent hydrogen, a cycloalkyl group with 1 to 6 carbon atoms or a —$(CH_2)OR^4$ group, in which z is 1, 2, 3, 4, 5 or 6 with $R^4$ being a linear or branched alkyl group with 1 to 4 carbon atoms, with the proviso that $R^2$ and $R^3$ cannot simultaneously be hydrogen.

The compounds of the general formula (I) preferably are selected from N-(2-methoxyethyl)-4-nitrophenylamine, N-(2-methoxyethyl)-2-methyl-4-nitrophenylamine, 4-(4-nitrophenyl)morpholine, N-(3-methoxypropyl)-4-nitrophenylamine, N-(3-methoxypropyl)-2-methyl-4-nitrophenylamine, 4-(2-methyl-4-nitrophenyl)-morpholine, N-cyclopropyl-4-nitrophenylamine, 4-nitro-N-((tetrahydrofuran-2-yl)methyl)-phenylamine, 2-methyl-4-nitro-N-(tetrahydrofuran-2-yl-methyl)-phenylamine and N-cyclopropyl-2-methyl-4-nitrophenylamine.

The dyes of formula (I) are used in the inventive dye compositions preferably in a total amount of 0.01 to 10% by weight and particularly in a total amount of 0.1% to 5% by weight.

The dyes of formula (I) can easily be synthesized from available precursors and not only have a good water solubility, but also a very good absorption behavior from anionic, cationic, amphoteric or nonionic carrier compositions. The coloring obtained has a very high resistance towards being washed out and towards perspiration and light radiation, as well as towards bases, such as ammonia and acids, such as phosphoric acid or reducing agents, such as ascorbic acid or sodium sulfite, so that their use in oxidative dye compositions is facilitated appreciably. In addition, the inventive dye compositions have a good shelf life and make possible intensively luminous yellow color shades, with possibilities for varying them in all gradations and nuances from a bright lemon yellow to an intensive dark yellow.

The inventive dye compositions can be used with and also without the addition of an oxidizing agent. In the former case, the usual developing and coupling substances are added.

If the dye composition is used without an oxidizing agent, it may contain, aside from the dyes of formula (I), further, known direct-dyeing dyes from the group comprising nitro, azo, anthraquinone and triphenylmethane dyes, either alone or in admixture with one another.

Example of suitable dyes, which are picked up directly, are 1,4-bis[(2-hydroxyethyl)amino]-2-nitrobenzene, 1-(2- hydroxyethyl)amino-2-nitro-4-[di(2-hydroxyethyl)amino]-benzene (HC Blue No. 2), 1-amino-3-methyl-4-[(2-hydroxyethyl)amino]-6-nitrobenzene (HC Violet No. 1), 4-[ethyl-(2-hydroxyethyl)-amino]-1-[(2-hydroxyethyl) amino]-2-nitrobenzene hydrochloride (HC Blue No. 12), 4-[di-(2-hydroxyethyl)amino]-1-[(2-methoxyethyl)amino]-2-nitrobenzene (HC Blue No. 11), 1-[(2,3-dihydroxypropyl) amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl) amino)-5-dimethylamino-benzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl) amino]-4-(2-hydroxyethoxy)-2-nitrobenzene (HC Orange No. 2), 4-(2,3-dihydroxypropoxy)-1-[(2-hydroxyethyl) amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl) amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl) amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]- 5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl) amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-fluoro-methylbenzene (HC Yellow No. 6), 1-chloro-2,4-bis[(2-hydroxyethyl) amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitro-benzamide (HC Yellow No. 15), 1,4-di[(2,3-dihydroxypropyl)amino]-9,10-anthraquinone, 1-[(2-hydroxyethyl)amino-4-methylamino-9,10-anthraquinone (CI61505; Disperse Blue No. 3), 2-[(2-aminoethyl)amino]-9,10-anthraquinone (HC Orange No., 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl) amino]-9,10-anthraquinone (HC Red No. 8), 1,4-diamino-2-methoxy-9,10-anthraquinone (CI62015; Disperse Red No. 11, Solvent Violet No. 26), 1,4-dihydroxy-5,8-bis[(2-hydroxyethyl)amino]-9,10-anthraquinone (CI62500; Disperse Blue No. 7, Solvent Blue No. 69), 9-(dimethylamino)-benzo[a]phenoxazin-7-ium chloride (CI51175; Basic Blue No. 6), di[4-(diethylamino)phenyl][4-(ethylamino) naphthyl]carbenium chloride (CI42595; Basic Blue No. 7), 3,7-di(dimethylamino)phenothiazin-5-ium chloride (CI52015; Basic Blue No. 9), di[4-(dimethylamino)phenyl] [4-(phenylamino)naphthyl]carbenium chloride (CI44045; Basic Blue No. 26), 2-[(4-(ethyl(2-hydroxyethyl)amino) phenyl)azo]-6-methoxy-3-methyl-benzothiazolium methyl sulfate (CI11154; Basic Blue No. 41), 8-amino-2-bromo-5-hydroxy-4-imino-6-[(3-(trimethylammonio)phenyl)amino]-1(4H)-naphthalenone chloride (CI56059; Basic Blue No. 99), bis[4-(dimethylamino)phenyl][4-(methylamino) phenyl]carbenium chloride (CI42535; Basic Violet No. 1), tris[4-(dimethylamino)phenyl]carbenium chloride (CI42555; Basic Violet No. 3), 2-[3,6-(diethylamino) dibenzopyranium-9-yl]-benzoic acid chloride (CI45170; Basic Violet No. 10), di-(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI12250; Basic Brown No. 16), 1-[(4-amino-2-nitrophenyl)azo]-7-(trimethylammonio)-2-naphthol chloride (Basic Brown No. 17), 1-[(4-amino-3-nitrophenyl)-azo]-7-(trimethylammonio)-2-naphthol chloride (CI12251; Basic Brown No. 17), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No., 22), 2-hydroxy-1-[(2-methoxyphenyl)azo]-7-(trimethylammonio)-naphthalene chloride (CI12245; Basic Red No. 76), 2-[2-((2,4-dimethoxyphenyl)amino)ethenyl]-1,3,3-trimethyl-3H-indol-1-ium chloride (CI48055; Basic Yellow No. 11). 3-methyl-1-phenyl-4-[(3-(trimethylammonio)phenyl) azo]-pyrazol-5-one chloride (CI12719; Basic Yellow No. 57), bis[4-(diethylamino)-phenyl]phenylcarbenium hydrogen sulfate (1:1) (CI42040); Basic Green No. 1), 1-[di(2-hydroxyethyl)amino]-3-methyl-4-[(4-nitrophenyl)azo]-benzene (CI11210, Disperse Red No. 17), 4-[(4-aminophenyl)azo]-1-[di(2-hydroxyethyl) amino]-3-methylbenzene (HC Yellow No. 7), disodium 2,6-diamino-3-[(pyridin-3-yl)azo]-pyridine, disodium 6-hydroxy-5-[(4-sulfophenyl)azo]-2-naphthalenesulfonate (CI15985; Food Yellow No. 3), disodium 2,4-dinitro-1-naphthol-7-sulfonate (CI10316; Acid Yellow No. 1; Food Yellow No. 1), 2-(indan-1,3-dion-2-yl) quinolinesulfonic acid (CI47005; Food Yellow No. 13; Acid Yellow No. 3), trisodium 5-hydroxy-1-(4-sulfophenyl)-4-[(4-sulfophenyl) azo]pyrazol-3-carboxylate (CI19140; Food Yellow No. 4; Acid Yellow No. 23), 9-(2-carboxyphenyl)-6-hydroxy-3H-xanthen-3-one (CI45350; Acid Yellow No. 73), sodium 5-[( 2,4-dinotrophenyl)amino]-2-phenylamino-benzosulfonate (CI10385; Acid Orange No. 3), sodium 4-[(2,4-dihydroxyphenyl)azo]-benzosulfonate (CI14270; Acid Orange No. 6), sodium 4-[(2-hydroxynaphth-1-yl)azo]-benzosulfonate (CI15510; Acid Orange No. 7), sodium 4-[(2,4-dihydroxy-3-[(2,4-dimethylphenyl)azo]-phenyl) azo]-benzosulfonate (CI20170; Acid Orange No. 24), disodium 4-hydroxy-3-[(4-sulfonaphth-1-yl)azo]-1-naphthalene sulfonate (CI14720; Acid Red No. 14), trisodium 6-hydroxy-5-[(4-sulfonaphth-1-yl)azo]-2,4-naphthalene disulfonate (CI16255; Ponceau 4R; Acid Red No. 18), trisodium 3-hydroxy-4-[(4-sulfonaphth-1-yl)azo]-2,7-naphthalene disulfonate (CI16185; Acid Red No. 27), disodium 8-amino-1-hydroxy-2-(phenylazo)-3,6-naphthalene disulfonate (CI17200; Acid Red No. 33), disodium 5-(acetylamino)-4-hydroxy-3-[(2-methylphenyl)azo]-2,7-naphthalene disulfonate (CI18065; Acid Red No. 35), disodium 2-(3-hydroxy-2,4-5,7-tetraioddibenzopyran-6-on-9-yl)-benzoate (CI45430; Acid Red No. 51), sodium N-[6-(diethylamino)-9-(2,4-disulfophenyl)-3H-xanthen-3-yliden]-N-ethylethaneammonium hydroxide inner salt (CI45100; Acid Red No. 52), disodium 8-[(4-phenylazo)phenyl)azo]-7-naphthol-1,3-disulfonate (CI27290; Acid Red No. 73), disodium 2',4',5',7'-tetrabromo-3'-6'-dihydroxyspiro[isobenzofuran-1(3H),9'-[9H]xanthen]-3-one (CI45380; Acid Red No. 87), disodium 2',4',5',7'-tetrabromo-4,5,6,7-tetrachloro-3',6'-dihydroxyspiro[isobenzofuran-1(3H),9'[9xanthen]-3-one (CI45410; Acid Red No. 92), disodium 3',6'-dihydroxy-4',5'-diiodospiro[isobenzofuran-1(3H),9'(9H)-xanthen]-3-one (CI45425; Acid Red No. 95), disodium (2-sulfophenyl)di[4-(ethyl((4-sulfophenyl)methyl)amino)-phenyl]-carbenium salt, betaine (CI42090); Acid Blue No. 9; FD&C Blue No. 1), sodium salt of 1,4-bis(2-sulfo-4-methylphenyl)amino-9,10-anthraquinone (CI 61570; Acid Green No. 25), monosodium internal salt of bis[4-(dimethylamino)phenyl]-(3,7-disulfo-2-hydroxynaphth-1-yl)carbenium (CI44090; Food Green No. 4; Acid Green No. 50), internal sodium salt of bis[4-(diethylamino)phenyl](2,4-disulfophenyl)carbenium (2:1) (CI42045; Food Blue No. 3; Acid Blue No. 1), internal calcium salt of bis[4-(dimethylamino)phenyl](5-hydroxy-2,4-disulfophenyl)carbenium (2:1) (CI42051; Acid Blue No. 3), sodium 1-amino-4-(cyclohexylamino)-9,10-anthraquinone-2-sulfonate (CI62045; Acid Blue No. 62), disodium 2-(1,3-dihydro-3-oxo-5-sulfo-2H-indol-2-ylidene)-2,3-dihydro-3-oxo-1H-indole-5-sulfonate (CI73015; Acid Blue No. 74), internal monosodium salt of 9-(2-carboxyphenyl)-3-[(2-methylphenyl)amino]-6-[(2-methyl-4sulfophenyl) amino]xanthylium (CI45190; Acid Violet No. 9), sodium salt of 1-hydroxy-4-[(methyl-2-sulfophenyl)-amino]-9,10-anthraquinone (CI60730; D&C Violet No. 2; Acid Violet No. 43), bis[3-nitro-4-[(4-phenylamino)3-sulfophenylamino]-phenyl]sulfone (CI10410; Acid Brown No. 13), disodium 5-amino-4-hydroxy-6-[(4-nitrophenyl)azo]-3-(phenylazo)-2,7-naphthalene disulfonate (CI20470; Acid Black No. 1), chromium complex of 3-hydroxy-4-[(2-hydroxynaphth-1-yl)azo]-7-nitro-1-naphthalenesulfonic acid (3:2) (CI15711; Acid Black No. 52), disodium 3-[(2,4-dimethyl-5-sulfophenyl)azo]-4-hydroxy-1-naphthalene-sulfonate (CI14700; Food Red No. 1; Ponceau SX; FD&C Red No. 4), tetrasodium 4-(acetylamino)-5-hydroxy-6-[(7-sulfo-4-[(4-sulfophenyl)azo]naphth-1-yl)azo]-1,7-naphthalene disulfonate (CI28440; Food Black No. 1), chromium complex of sodium 3-hydroxy-4-(3-methyl-5-oxo-1-phenyl-4,5-dihydro-1H-pyrazole-4-ylazo)-naphthalene-1-sulfonate (Acid Red No. 195).

The above-named nitro, azo, anthraquinone or triphenylmethane dyes, which are picked up directly, may be contained in a total amount of about 0.01 to 4% by weight, the total content of non-oxidative dyes preferably amounting to about 0.01 to 8% by weight and particularly to 0.1 to 5% by weight.

The inventive dye compositions based on compounds of the general formula (I), as well as optionally dyes, which are picked up directly, are preferably in the form of a solution, particularly an aqueous-alcoholic solution. Further preferred forms of compositions of the invention are creams, gels or emulsions. It is also possible to dispense these materials from a pressurized container with the help of an atomizer or different suitable pumping devices or spraying devices or in admixture with conventional, liquefied blowing agents under pressure as an aerosol spray or an aerosol foam.

The pH of the dye compositions according to the invention is within the range of 3 to 12 and particularly within the range of 8 to 11.5. Preferably, the pH is adjusted with ammonia to alkaline values. However, it can also be adjusted to such values with organic amines, such as monoethanolamine or triethanolamine. For adjustments to an acidic pH, diluted organic or inorganic acids, such as hydrochloric, sulfuric, phosphoric, ascorbic or lactic acid can be used, depending on the pH desired.

These dye compositions are used for dyeing hair in the usual manner by applying an amount of the dye composition, sufficient for the dyeing, on the hair, with which it remains in contact for a time, preferably 15 to 30 minutes. Subsequently, the hair is rinsed with water, then optionally with an aqueous solution of a weak organic acid and subsequently dried. As weak organic acid, acetic, citric or tartaric acid, for example, can be used in the form of a dilute aqueous solution.

The dye composition, which is described above and to which no oxidizing agent has been added, may furthermore contain natural or synthetic polymers or modified polymers of natural origin, which are customarily used for cosmetic materials. As a result, strenghthening of the hair is achieved simultaneously with the coloring. Such materials generally are feferred to as shade fortifier or color fortifier.

Of the synthetic polymers, known for this purpose in cosmetics, polyvinylpyrrolidone, polyvinyl acetate, polyvinyl alcohol, polyacrylate compounds, such as polyacrylic acid or polymethacrylic acid, basic polymers of esters of polyacrylic acid, polymethacrylic acid and amino alcohols, for example, their salts or quatemization products, polyacrylonitrile, polyvinyl acetate and copolymers of such compounds, such as polyvinyl pyrrolidone-vinyl acetate are, for example, mentioned. As natural polymers or modified natural polymers, chitosan (deacetylated chitin) or chitosan derivatives may, for example, be used. The aforementioned polymers may be contained in the inventive materials in amounts, customary for such materials, especially in amounts of about 1 to 5% by weight. The pH of the inventive shade or color fortifier is about 6 to 9.

The hair dye composition according to the invention with additional strength is used in the known and conventional manner by moistening the hair with the fortifier, setting the hair for the hair style and subsequently drying.

Of course, the hair dye composition without oxidizing agent, described above, may optionally contain further additives, which are customary in hair dye compositions, such as care materials, wetting agents, thickeners, plasticizers, preservatives and perfume oils, as well as other conventional additives, listed below for oxidation hair dye compositions.

As already mentioned, hair dye compositions, for which the addition of an oxidizing agent is required, are also an object of the present invention. Aside from the dyes of the general formula (I), as well as, optionally, further dyes, which are picked up directly by the hair and comprise the group consisting of nitro, azo, anthraquinone and triphenylmethane dyes, these dye compositions additionally contain known oxidation dye precursors, which require an oxidative treatment (developer and coupler substances).

Examples of developers are 1,4-diamino-benzene (p-phenylenediamine), 1,4-diamino-2-methyl-benzene (p-toluylenediamine), 1,4-diamino-2,6-dimethyl-benzene, 1,4-diamino-2,5-dimethyl-benzene, 1,4-diamino-2,3-dimethyl-benzene, 2-chloro-1,4-diaminobenzene, 4-phenylamino-aniline, 4-dimethylamino-aniline, 4-diethylamino-aniline, 4-[di(2-hydroxyethyl)amino]- aniline, 4-[(2-methoxyethyl)amino]-aniline, 4-[(3-hydroxypropyl)amino]-aniline, 1,4-diainino-2-(2-hydroxyethyl)-benzene, 1,4-diamino-2-(1-methylethyl)-benzene, 1,3-bis[(4-aminophenyl)(2-hydroxyethyl)amino]-2-propanol, 1,8-bis(2,5-diaminophenoxy)-3,6-dioxaoctane, 4-amino-phenol, 4-amino-3-methyl-phenol, 4-methylamino-phenol, 4-amino-2-(aminomethyl)-phenol, 4-amino-2-[(2-hydroxyethyl)-amino]methyl-phenol, 4-amino-2-(methoxymethyl)-phenol, 4-amino-2-(2-hydroxyethyl)-phenol, 5-amino-salicylic acid, 2,5-diamino-pyridine, 2,4,5,6-tetraamino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-amino-phenol, 2-amino-6-methyl-phenol, 2-amino-5-methyl-phenol. The developer substances named can be used individually or also in admixture with one another.

Examples of couplers are 5-((2-hydroxyethyl)amino)-2-methoxyaniline, N-(3-dimethylamino-phenyl)-urea, 2,6-diamino-pyridine, 2-amino-4-[(2-hydroxyethyl)amino]-anisole, 2,4-diamino-1-fluoro-5-methyl-benzene, 2,4-diamino-1-methoxy-5-methyl-benzene, 2,4-diamino-1-ethoxy-5-methyl-benzene, 2,4-diamino-1-(2-hydroxyethoxy)-5-methyl-benzene, 2,4-di[(2-hydroxyethyl)amino]-1,5-dimethoxy-benzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diamino-benzene, 2,4-diamino-1-(2-hydroxyethoxy)-benzene, 2,4-diamino-1,5-di(2-hydroxyethoxy)-benzene, 1-(2-aminoethoxy)-2,4-diamino-benzene, 2-amino-1-(2-hydroxyethoxy)-4-methylamino-benzene, 2,4-diaminophenoxy-acetic acid, 3-[di(2-hydroxyethyl)amino]-aniline, 4-amino-2-di[(2-hydroxyethyl)amino]-1-ethoxy-benzene, 5-methyl-2-(1-methylethyl)-phenol, 3-[(2-hydroxyethyl)amino]-aniline, 3-[(2-aminoethyl)amino]-aniline, 1,3-di(2,4-diaminophenoxy)-propane di(2,4-diaminophenoxy)-methane, 1,3-diamino-2,4-dimethoxy-benzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichloro-phenol, 5-amino-2,4-dichloro-phenol, 3-amino-2-methyl-phenol, 3-amino-2-chloro-6-methyl-phenol, 3-amino-phenol, 2-[(3-hydroxyphenyl)amino]-acetamide, 5-[(2-hydroxyethyl)amino]-2-methyl-phenol, 3-[(2-hydroxyethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl) amino]-2-methyl-phenol, 3-[(2,3-dihydroxypropyl)amino]-2-methyl-phenol, 3-[(2-hydroxyethyl)amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol-acetate, 1,3-dihydroxy-benzene, 1-chloro-2,4-dihydroxy-benzene, 2-chloro-1,3-dihydroxy-benzene, 1,2-dichloro-3,5-dihydroxy-4-methyl-benzene, 1,5-dichloro-2,4-dihydroxy-benzene, 1,3-dihydroxy-2-methyl-benzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diamino-benzoic acid, 3,4-dihydro-6-hydroxy-1,4-(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indolin, 5-hydroxy-indole, 6-hydroxy-indole, 7-hydroxy-indole, 2,3-indolindione. The coupler substances named can be used individually as well as in admixture with one another.

As particularly preferred compounds, especially 1,4-diamino-2-methyl-benzene, 4-[(di(2-hydroxyethyl)amino]-aniline, 1,4-diamino-2-(2-hydroxyethyl)-benzene, 4-amino-3-methylphenol, 4-amino-2-(aminomethyl)-phenol, 2,4,5,6-tetraaminopyrimidine, 4,5-diamino-1-(2-hydroxy-ethyl)-1H-pyrazole, 4-chlororesorcinol, 3-aminophenol, 5-hydroxy-1,3-benzodioxol, 5-amino-1,3-benzodioxol, 5-((2'-hydroxyethyl)-amino)-1,3-benzodioxol, 2-amino-4-[(2-hydroxyethyl)amino]-anisole, 2,4-diamino-1-fluoro-5-methyl-benzene, 5-amino- 2-methylphenol, 1,3-di(2,4-diaminophenoxy)-propane, 3-amino-2-chloro-6-methyl-phenol, 1-naphthol, 1,3-dihydroxy-benzene, 1,3-dihydroxy-2-methyl-benzene, 2,4-diamino-1-(2-hydroxyethoxy)-benzene, 5-((2-hydroxyethyl)amino)-2-methoxyaniline and 5-((3-hydroxypropyl)amino)-2-methylphenol, come into consideration.

Further oxidation dyes, known and used for coloring hair, are described, for example, in the book by E. Sagarin, "Cosmetics, Science and Technology" (1957), Interscience Publishers Inc., New York, pages 503 ff, as well as in the book by H. Janistyn, "Handbuch der Kosmetika und Riechstoffe (Handbook of Cosmetics and Fragrances), volume 3" (1973), pages 388 to 397.

Very good natural blonde and brown shades as well as fashionable nuances can be produced with combinations of oxidation dyes and the dyes of formula (I).

The inventive dyes of formula (I) are contained in the coloring agents, to which an oxidation agent has been added, preferably in an amount of 0.01 to 4.0% by weight and especially of 0.02 to 2.0% by weight, the total content of non-oxidative dyes preferably amounting to about 0.1 to 5% by weight.

The total concentration of oxidation dye precursor in the inventive oxidation coloring agent is between about 0.1 and 10% by weight, an amount of 0.2 to 2% by weight being preferred.

The pH of the oxidation dye composition can be adjusted to an acidic, a neutral or a basic value (pH=3 to 12), a pH of 6 to 12 and particularly a pH of about 8.0 to 11.5 being preferred. The pH is adjusted to the desired alkaline value usually by ammonia; however, other organic amines, such as monoethanolamine or triethanolamine or inorganic bases, such as sodium hydroxide and potassium hydroxide, can also be used. The pH is adjusted to an acidic value with organic acids, such as citric, glycolic, lactic, malic, ascorbic or tartaric acid.

As oxidation agent for developing the coloration, primarily hydrogen peroxide and its addition compounds come into consideration. The inventive oxidation dye composition may be prepared in a form, which is identical to that of the inventive non-oxidative dye composition, the oxidation dye composition preferably being in the form of a cream or a gel.

Conventional additives in solutions, creams, emulsions or gels are, for example, solvents such as water, lower molecular weight aliphatic monohydric or multihydric alcohols, their esters and ethers, such as alkanols, particularly with 1 to 4 carbon atoms, such as ethanol, propanol or isopropanol, butanol, isobutanol, dihydric and trihydric alcohols, especially those with 2 to 6 carbon atoms, such as ethylene glycol, propylene glycol, 1,3-dihydroxypropane, 1,4-dihydroxybutane, 1,5-dihydroxypentane, 1,6-dihydroxyhexane, 1,2,6-trihydroxyhexane, glycerin, diethylene glycol, dipropylene glycol, polyalkylene glycols, such as triethylene glycol, polyethylene glycol, tripropylene glycol, polypropylene glycol, lower molecular weight alkyl ethers of multihydric alcohols, such as ethylene glycol monomethyl ether or ethylene glycol monoethyl ether or ethylene glycol monopropyl ether or ethylene glycol monobutyl ether, diethylene glycol monomethyl ether or diethylene glycol monoethyl ether, triethylene glycol monomethyl ether or triethylene glycol monoethyl ether, ketones and keto alcohols, particularly those with 3 to 7 carbon atoms, such as acetone, methyl ethyl ketone, diethyl ketone, methyl isobutyl ketone, methyl phenyl ketone, cyclopentanone, cyclohexanone and diacetone alcohol, ethers, such as dibutyl ether, tetrahydrofiran, dioxane, diisopropyl ether, esters, such as ethyl formate, methyl formate, methyl acetate, ethyl acetate, propylene acetate, butyl acetate, phenyl acetate ethylene glycol monoethyl ether acetate and hydroxyethyl acetate, amides, such as dimethylformamide and dimethylacetamide, N-methylpyrrolidone as well as urea, tetramethylurea and thiodiglycol.

Furthermore, the inventive dye compositions may contain wetting agents or emulsifiers from the classes of anionic, cationic, amphoteric, nonionic or zwitterionic surface active substances, such as fatty alcohol sulfates, alkanesulfonates, alkylbenzenesulfonates, alkyltrimethylammonium salts, alkylbetaines, α-olefinsulfonates, ethoxylated fatty alcohols, ethoxylated nonyiphenols, fatty acid alkanolamines, ethoxylated fatty esters, fatty alcohol polyglycol ether sulfates, alkyl polyglucosides, thickening agents, such as higher molecular weight fatty alcohols, starch, algenates, bentonites, cellulose derivatives, Vaseline, paraffin oil and fatty acids, water-soluble polymeric thickening agents, such as natural types of gum, guar gum, xanthan gum, carob core flour, pectin, dextran, agar, amylose, amylopectin, dextrins, clays or fully synthetic hydrocolloids, such as polyvinyl alcohol, as well as care materials, such as lanolin derivatives, cholesterol, pantothenic acid, water soluble cationic polymers, protein derivatives, provitamins, vitamins, plant extracts, sugar and betaine, auxiliary materials, such as moisturizers, electrolytes, antioxidants, fatty amides, sequestering agents, film-forming agents and preservatives. Aside from water, a water-soluble organic solvent or a mixture of such solvents, as well as a water/solvent mixture may also be used.

The components mentioned are used in amounts customary for such purposes. For example, the wetting agents and emulsifiers are used in concentrations of about 0.5 to 30% by weight, the thickeners in an amount of about 0.1 to 25% by weight and the care materials in an amount of about 0.1 to 5% by weight.

When used for the oxidative coloring of hair, the dye composition, described above, is mixed immediately before use with an oxidizing agent and an amount, sufficient for the hair coloring treatment and depending on the thickness of the hair, generally from 60 to 200 g of this mixture, is applied to the hair. As oxidizing agent for developing the hair coloring, mainly hydrogen peroxide or its addition compounds with urea, melamine or sodium borate come into consideration in the form of 3% to 12% and preferably 6% aqueous solutions.

If a 6% hydrogen peroxide solution is used as oxidizing agent, the ratio by weight of dye composition to oxidizing agent is 5:1 to 1:2 and preferably 1:1. Larger amounts of oxidizing agent are used especially when the dye concentrations in the dye composition are higher or if a strong bleaching of the hair is intended at the same time.

The dye solution is allowed to act on the hair at 20° to 50° C. for about 10 to 45 minutes and preferably at 40° C. for 40 minutes. The hair is then rinsed with water and dried. Optionally, at the conclusion of the rinsing, the hair is washed with a shampoo, rinsed and subsequently dried.

Especially when coloring hair, the dye composition according to the invention leads to dyed colors with excellent fastness properties, especially with respect to light fastness, wash fastness and perspiration fastness. The high color intensity and the purity of the color of the achievable colorations are remarkable even after a three-month storage. Finally, gray hair, which has not been damaged chemically, can also be tinted without problems and with good covering power with the dye composition described. Independently of the different structure of the hair, the colorations obtained are uniform and well reproducible. Depending on their composition, the dye compositions are used either in conjunction with and also without an oxidizing agent.

The dye compositions according to the invention, based on compounds of formula (I), are suitable particularly for dyeing keratin fibers, such as wool, furs or hair, especially human hair. It is, however, also readily possible to dye other natural fibers such as cotton, jute, sisal, linen or silk, modified natural fibers such as regenerated cellulose, nitrocellulose, alkylcellulose, hydroxyalkylcellulose or acetylcellulose, or synthetic fibers, such as polyamide fibers, polyurethane fibers and polyester fibers with these dye compositions.

The following examples are intended to explain the object of the invention without limiting it to these.

EXAMPLES

SYNTHESIS EXAMPLES

Example 1

Synthesis of N-(2-methoxyethyl)-4-nitro-phenylamine

1-Fluoro-4-nitrobenzene (28.2 g, 0.2 moles) is refluxed for 5 hours with 87.1 g (1.16 moles) of 1-amino-2-methoxyethane. At the end of the reaction (checked by thin-layer chromatography; ethyl acetate), the reaction product is poured onto 500 g of ice/water. A yellow dye is precipitated. The product is recrystallized from ethanol and forms fine yellow needles with a melting point of 85°–87° C.

Yield: 97% of the theoretical. $^1$H-NMR (60 MHz, DMSO-$d_6$): 1.13 (t, $CH_3$; 3H); 3.34 (s, CH, 1H): 3.93 (q, $CH_2$, 2H); 7.55 (d, H-(C6), 1H); 7.95 (dxd, H-C(5), 1H); 8.27 (d, H-C(3), 1H). IR Spectrum (Film): 3110 w, 2987 m, 2250 w, 1749 vs, 1610 s, 1542 s, 1468 s, 1350 s, 1261 s, 1216 s, 1026 s; MS (m/z, rel. intensity): 196 (50, $M^+$), 180 (14, $CH_4^+$), 151 (63, —$NO_2$), 135 (9), 119 (6), 105 (77), 104 (13); TLC (3:1 hexane/ethyl acetate): $R_f$=0.38; Elementary Analysis: $C_9H_{12}O_3N_2$ (molecular weight=196.21);

|  | C | H | N |
|---|---|---|---|
| calculated: | 55.08 | 6.17 | 14.28 |
| found: | 55.21 | 6.14 | 14.33 |

Example 2

Synthesis of N-(2-methoxyethyl)-2-methyl-4-nitrophenylamine

1-Fluoro-2-methyl-4-nitrobenzene (26 g, 0.17 moles) is refluxed for 5 hours with 73 g (1 mole) of 1-amino-2-methoxyethane. After that, the reaction product is poured onto 500 g of ice/water. The solid obtained is filtered off and recrystallized from ethanol. Small yellow prisms with a melting point of 97°–100° C. are obtained.

Yield: 74% of the theoretical. $^1$H-NMR (60 MHz, DMSO-$d_6$): 1.13 (t, $CH_3$; 3H); 3.34 (s, CH, 1H): 3.93 (q, $CH_2$, 2H); 7.55 (d, H-(C6), 1H); 7.95 (dxd, H-C(5), 1H); 8.27 (d, H-C(3), 1H); IR Spectrum (Film): 3110 w, 2987 m, 2250 w, 1749 vs, 1610 s, 1542 s, 1468 s, 1350 s, 1261 s, 1216 s, 1026 s; MS (m/z, rel. intensity): 210 (30, M$^+$), 165 (100, $-NO_2$), 119 (45, $C_7H_7$), 118 (10), 107 (5), 104 (8), 89 (9); TLC (3:1 hexane/ethyl acetate): $R_f$=0.38; Elementary Analysis: $C_{10}H_{14}O_2N_3$ (210.23);

|  | C | H | N |
| --- | --- | --- | --- |
| calculated: | 57.12 | 6.72 | 13.33 |
| found: | 57.16 | 6.71 | 13.40 |

Example 3
Synthesis of N-(3-Methoxypropyl)-4-nitro-phenylamine

1-Fluoro-4-nitrobenzene (10 g, 70.8 mmoles) is refluxed for 5 hours with 36.5 g (410 mmoles) of 3-methoxypropylamine. After that, the reaction product is poured onto 400 g of ice/water and the dye obtained is filtered off. A yellow dye with a melting point of 57°–59° C. is obtained.

Yield: 98% of the theoretical.

Example 4
Synthesis of 4-(4-Nitro-phenyl)-morpholine

1-Fluoro-4-nitrobenzene (10 g, 70.9 mmoles) is refluxed for 5 hours with 35.7 g (0.41 moles) of morpholine. After that, the reaction product is poured onto 400 g of ice/water and the solid obtained is filtered off. After a recrystallization from ethanol, a dark yellow, finely pulverized dye is obtained with a melting point of 152°–154° C.

Yield: 98% of the theoretical.

Example 5
Synthesis of N-(3-Methoxypropyl)-2-methyl-4-nitro-phenylamine

1-Fluoro-2-methyl-4-nitrobenzene (10 g, 0.07 moles) is refluxed for 5 hours with 36.5 g (0.4 moles) of 1-amino-2-methoxypropane. After that, the reaction product is poured onto 350 g of ice/water and the solid obtained is filtered off. After recrystallization from ethanol, a yellow, crystalline powder with a melting point of 26°–28° C. is obtained.

Yield: 60% of the theoretical.

Example 6
Synthesis of 4-(2-Methyl-4-nitro-phenyl)-morpholine

1-Fluoro-2-methyl-4-nitrobenzene (10 g, 0.07 moles) is refluxed for 5 hours with 35.7 g (0.4 moles) of 1-amino-2-methoxyethane. After that, the reaction product is poured onto 350 g of ice/water and the dye obtained is filtered off. Recrystallization from ethanol results in a yellow, crystalline powder with a melting point of 147°–150° C.

Yield: 70% of the theoretical.

Example 7
Synthesis of N-Cyclopropyl-4-nitro-phenylamine

1-Fluoro-4-nitrobenzene (3.5 g, 24.8 mmoles) is refluxed for 5 hours with 8.1 g (0.14 moles) of cyclopropylamine. After that, the reaction product is poured onto 250 g of ice/water and the precipitate is filtered off. After recrystallization from ethanol, a yellow solid with a melting point of 126°–128° C. is obtained.

Yield: 75% of the theoretical.

Example 8
Synthesis of 4-Nitro-N-((tetrahydrofuran-2-yl) methylphenylamine

1-Fluoro-4-nitrobenzene (10 g, 70.9 mmoles) is refluxed for 5 hours with 41.5 g (0.41 moles) of tetrahydrofurfurylamine. After that, the reaction product is poured onto 400 g of ice/water and the solid obtained is recrystallized from water. A dark yellow, coarsely grained dye with a melting point of 65°–67° C. is obtained.

Yield: 100% of the theoretical.

Example 9
Synthesis of 2-Methyl-4-nitro-N-(tetrahydrofuran-2-yl-methyl)-phenylamine 1-Fluoro-2-methyl-4-nitrobenzene (11 g, 70.9 mmoles) is refluxed for 5 hours with 41.5 g (0.41 moles) of tetrahydrofurfurylamine. After that, the reaction product is poured onto 400 g of ice/water and the solid obtained is filtered off. Recrystallization from ethanol/water results in a yellow, grainy dye with a melting point of 56°–58° C.

Yield: 80% of the theoretical.

Example 10
Synthesis of N-Cyclopropyl-2-methyl-4-nitro-phenylamine

1-Fluoro-2-methyl-4-nitrobenzene (3.7 g, 24.8 mmoles) is refluxed for 5 hours with 8.1 g (0.14 moles) of cyclopropylamine. After that, the reaction product is poured onto 250 g of ice/water and the solid obtained is recrystallized from ethanol. A yellow solid with a melting point of 35°–37° C. is obtained.

Yield: 75% of the theoretical.

EXAMPLES OF DYE COMPOSITIONS

Example 11
Hair Dye Composition with N-(2-Methoxyethyl)-4-nitro-phenylamine

| | |
| --- | --- |
| 0.49 g | N-(2-methoxyethyl)-4-nitro-phenylamine |
| 10.00 g | isopropanol |
| 10.00 g | sodium salt of lauryl alcohol diglycol ether sulfate (28% aqueous solution) |
| ad 100.00 g | water |

The above dye-containing mass is mixed immediately before use to form the ready-to-use hair dye composition. The pH is adjusted once with lactic acid (to an acidic pH of 5) and once with dilute ammonia solution (to an alkaline pH of 8). Bleached hair samples are then treated for 40 minutes at a temperature of 40° C. with respective portions of the hair dye composition, one acidic, the other basic. Subsequently, the hair is rinsed with water and dried. An intensive lemon-yellow color results after the acidic as well as after the basic treatment. The dyed hair color obtained lasts up to five hair washings or a three-week exposure to sunlight without a noticeable loss in intensity.

Example 12
Hair Dye Composition with N-(2-Methoxyethyl)-2-methyl-4-nitro-phenylamine

| | |
| --- | --- |
| 0.525 g | N-(2-methoxyethyl)-2-methyl-4-nitro-phenylamine |
| 10.000 g | isopropanol |
| 10.000 g | sodium salt of lauryl alcohol diglycol ether sulfate |

-continued

| | |
|---|---|
| | (28% aqueous solution) |
| ad 100.000 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair samples are then treated for 40 minutes at a temperature of 40° C. with respective portions of the hair dye composition, one acidic, the other basic. Subsequently, the hair is rinsed with water and dried.

An intensive corn-yellow color results after the acidic as well as after the basic treatment. The dyed hair color obtained lasts up to five hair washings or a three-week exposure to sunlight without a noticeable loss in intensity.

Example 13
Hair Dye Composition with N-(3-Methoxypropyl)-4-nitro-phenylamine

| | |
|---|---|
| 0.525 g | N-(3-methoxypropyl)-4-nitro-phenylamine |
| 10.000 g | isopropanol |
| 10.000 g | sodium salt of lauryl alcohol diglycol ether sulfate (28% aqueous solution) |
| ad 100.000 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair samples are then treated for 40 minutes at a temperature of 40° C. with respective portions of the hair dye composition, one acidic, the other basic. Subsequently, the hair is rinsed with water and dried.

An intensive yellow color results after the acidic as well as after the basic treatment. The color obtained lasts up to five hair washings or a three-week exposure to sunlight without a noticeable loss in intensity.

Example 14
Hair Dye Composition with 4-(4-Nitro-phenyl)-morpholine

| | |
|---|---|
| 0.52 g | 4-(4-nitro-phenyl)-morpholine |
| 10.00 g | isopropanol |
| 10.00 g | sodium salt of lauryl alcohol diglycol ether sulfate (28% aqueous solution) |
| ad 100.00 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair samples are then treated for 40 minutes at a temperature of 40° C. with respective portions of the hair dye composition, one acidic, the other basic. Subsequently, the hair is rinsed with water and dried.

An intensive dark yellow color results after the acidic as well as after the basic treatment. The color obtained lasts up to five hair washings or a three-week exposure to sunlight without a noticeable loss in intensity.

Example 15
Hair Dye Composition with N-(3-methoxypropyl)-2-methyl-4-nitro-phenylamine

| | |
|---|---|
| 0.56 g | N-(3-methoxvpropyl)-2-methyl-4-nitro-phenylamine |
| 10.00 g | isopropanol |
| 10.00 g | sodium salt of lauryl alcohol diglycol ether sulfate (28% aqueous solution) |
| ad 100.00 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair samples are then treated for 40 minutes at a temperature of 40° C. with the respective portions of the hair dye composition, one acidic, the other basic. Subsequently, the hair is rinsed with water and dried.

An intensive yellow coloration results after the acidic as well as after the basic treatment. The coloration obtained survives up to five hair washings or a three-week exposure to sunlight without a noticeable loss in intensity.

Example 16
Hair Dye Composition with 4-(2-methyl-4-nitro-phenyl)-morpholine

| | |
|---|---|
| 0.555 g | 4-(2-methyl-4-nitro-phenyl)-morpholine |
| 10.000 g | isopropanol |
| 10.000 g | sodium salt of lauryl alcohol diglycol ether sulfate (28% aqueous solution) |
| ad 100.000 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair or wool or cotton samples are then treated for 40 minutes at a temperature of 40° C. with respective portions of the hair dye composition, one acidic, the other basic. Subsequently, the fibers are rinsed with water and dried.

An egg yellow color results after the acidic as well as after the basic treatment. The color obtained by the dyeing lasts up to five hair washings or a three-week exposure to sunlight without a noticeable loss in intensity.

Example 17
Hair Dye Composition with N-cyclopropyl-4-nitro-phenylamine

| | |
|---|---|
| 0.445 g | N-cyclopropyl-(4-nitro-phenyl)amine |
| 10.000 g | isopropanol |
| 10.000 g | sodium salt of lauryl alcohol diglycol ether sulfate (28% aqueous solution) |
| ad 100.000 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair samples are then treated for 40 minutes at a temperature of 40° C. with the respective portions of the hair dye composition, one acidic, the other basic. Subsequently, the hair is rinsed with water and dried.

An intensive signal yellow color results after the acidic as well as after the basic treatment. The color obtained lasts up to five hair washings or a three-week exposure to sunlight without a noticeable loss in intensity.

Example 18
Hair Dye Composition with 4-nitro-N-((tetrahydrofuran-2-yl)methyl)-phenylamine

| | |
|---|---|
| 0.48 g | 4-nitro-N-((tetrahydrofuran-2-yl)methyl)-phenylamine |
| 10.00 g | isopropanol |
| 10.00 g | sodium salt of lauryl alcohol diglycol ether sulfate (28% aqueous solution) |
| ad 100.00 g | water |

The ready-for-use hair dye composition is produced immediately before use by mixing the remaining components with water. The pH is adjusted once with lactic acid (to an acidic pH of 5) and once with dilute ammonia solution (to an alkaline pH of 8). Bleached hair or wool or cotton samples are then treated for 40 minutes at a temperature of 40° C. with the respective portions of the hair dye composition, one acidic, the other basic. Subsequently, the fibers are rinsed with water and dried.

An intensive dark yellow color results after the acidic as well as after the basic treatment. The color obtained lasts up to five hair washings or a three-week exposure to sunlight without a noticeable loss in intensity.

Example 19
Hair Dye Composition with 2-methyl-4-nitro-N-((tetrahydrofuran-2-yl)methyl)-phenylamine

| | |
|---|---|
| 0.59 g | 2-methyl-4-nitro-N-((tetrahydrofuran-2-yl)methyl)-phenylamine |
| 10.00 g | isopropanol |
| 10.00 g | sodium salt of lauryl alcohol diglycol ether sulfate (28% aqueous solution) |
| ad 100.00 g | water |

The pH of the hair dye composition is adjusted once with lactic acid (to an acidic pH of 5) and once with dilute ammonia solution (to an alkaline pH of 8). Bleached hair samples are then treated for 40 minutes at a temperature of 40° C. with the respective portions of the hair dye composition, one acidic, the other basic. Subsequently, the hair is rinsed with water and dried.

A mustard yellow dyed hair color results after the acidic as well as after the basic treatment. The color obtained lasts up to five hair washings or a three week exposure to sunlight without a noticeable loss in intensity.

Example 20
Hair Dye Composition with N-cyclopropyl-2-methyl-4-nitro-phenylamine

| | |
|---|---|
| 0.48 g | N-cyclopropyl-2-methyl-4-nitro-phenylamine |
| 10.00 g | isopropanol |
| 10.00 g | sodium salt of lauryl alcohol diglycol ether sulfate (28% aqueous solution) |
| ad 100.00 g | water |

The pH of the hair dye composition is adjusted once with lactic acid (to an acidic pH of 5) and once with dilute ammonia solution (to an alkaline pH of 8). Bleached hair samples are then treated for 40 minutes at a temperature of 40° C. with the respective portions of the hair dye composition, one acidic, the other basic. Subsequently, the hair is rinsed with water and dried.

An intensive yellow coloration results after the acidic as well as after the basic treatment. The coloration obtained survives up to five hair washings or a three-week exposure to sunlight without a noticeable loss in intensity.

Example 21
Oxidizing Hair Dye Composition in Cream Form

| | |
|---|---|
| 0.2 g | N-(2-methoxyethyl)-2-methyl-4-nitro-phenylamine |
| 15.0 g | cetyl alcohol |
| 3.5 g | sodium salt of lauryl alcohol diglycol ether sulfate (28% aqueous solution) |
| 0.4 g | sodium sulfite |
| 0.1 g | 3-aminophenol |
| 0.2 g | 1,3-dihydroxy-2-methylbenzene |
| 0.4 g | 1,4-diamino-2-methylbenzene |
| 40.0 g | ammonia (25% aqueous solution) |
| ad 100.0 g | water, desalinated |

The above hair dye composition (50 g) is mixed immediately before use with 50 g of hydrogen peroxide solution (6% aqueous solution) and the resulting mixture is applied onto the bleached hair. After a period of 30 minutes, the hair is rinsed with water, shampooed and dried. The dyed hair has a brown color.

Example 22
Oxidizing Hair Dye Composition in Cream Form

| | |
|---|---|
| 0.03 g | N-(2-methoxyethyl)-2-methyl-4-nitro-phenylamine |
| 23.00 g | cetyl alcohol |
| 10.00 g | sodium salt of lauryl alcohol diglycol ether sulfate (28% aqueous solution) |
| 0.30 g | ascorbic acid |
| 0.40 g | sodium sulfite |
| 0.03 g | 3-aminophenol |
| 0.29 g | 1,3-dihydroxybenzene |
| 0.03 g | 1,3-dihydroxy-2-methylbenzene |
| 0.60 g | 1,4-diamino-2-methylbenzene |
| 0.01 g | sodium hydroxide |
| 0.40 g | isopropyl alcohol |
| 7.60 g | ammonia (25% aqueous solution) |
| ad 100.00 g | water, desalinated |

The above hair dye composition (50 g) is mixed immediately before use with 50 g of hydrogen peroxide solution (6% aqueous solution) and the resulting mixture is applied onto the bleached hair. After a period of 30 minutes, the hair is rinsed with water, shampooed and dried. The hair, so treated, has a natural light brown color.

Example 23
Oxidizing Hair Dye Composition in Cream Form 0.03 g N-(2-methoxyethyl)-2-methyl-4-nitro-phenylamine

| | |
|---|---|
| 0.03 g | N-(2-methoxyethyl)-2-methyl-4-nitro-phenylamine |
| 23.00 g | cetyl alcohol |
| 10.00 g | sodium salt of lauryl alcohol diglycol ether sulfate (28% aqueous solution) |
| 0.30 g | ascorbic acid |
| 0.40 g | sodium sulfite |
| 0.02 g | 4-amino-3-methylphenol |
| 0.03 g | 1,4-diamino-2-(hydroxyethyl)benzenesulfate (1:1) |

-continued

| | | |
|---|---|---|
| 0.01 g | 1,3-di(2,4-diaminophenoxy)-propane tetrahydrochloride | |
| 0.01 g | 5-amino-2-methylphenol | |
| 0.02 g | 5-((2-hydroxyethyl)amino)-2-methoxyaniline sulfate (1:1) | |
| 0.01 g | 1,3-diamino-4-(2-hydroxyethoxy)-benzene | |
| 0.01 g | 4-amino-2-(aminomethyl)phenol dihydrochloride | |
| 0.02 g | 5-amino-2-methylphenol | |
| 0.03 g | 3-aminophenol | |
| 0.29 g | 1,3-dihydroxybenzene | |
| 0.03 g | 1,3-dihydroxy-2-methylbenzene | |
| 0.60 g | 1,4-diamino-2-methylbenzene | |
| 0.01 g | sodium hydroxide | |
| 0.40 g | isopropyl alcohol | |
| 7.60 g | ammonia (25% aqueous solution) | |
| ad 100.00 g | water, desalinated | |

The above hair dye composition (50 g) is mixed immediately before use with 50 g of hydrogen peroxide solution (6% aqueous solution) and the resulting mixture is applied onto the bleached hair. After a period of 30 minutes, the hair is rinsed with water, shampooed and dried. A brown hair color is obtained.

Example 24
Oxidizing Hair Dye Composition in Cream Form

| | |
|---|---|
| 0.03 g | N-(2-methoxyethyl)-4-nitro-phenylamine |
| 23.00 g | cetyl alcohol |
| 10.00 g | sodium salt of lauryl alcohol diglycol ether sulfate (28% aqueous solution) |
| 0.30 g | ascorbic acid |
| 0.40 g | sodium sulfite |
| 0.03 g | 1,4-diamino-2-(hydroxyethyl)benzenesulfate (1:1) |
| 0.01 g | 1,3-di(2,4-diaminophenoxy)-propane tetrahydrochloride |
| 0.02 g | 5-((2-hydroxyethyl)amino)-2-methoxyanilinesulfate (1:1) |
| 0.01 g | 1,3-diamino-4-(2-hydroxyethoxy)-benzene |
| 0.01 g | 4-amino-2-(aminomethyl)phenol dihydrochloride |
| 0.01 g | 2,4-diamino-1,5-di(2-hydroxyethoxy)-benzene |
| 0.01 g | 4-amino-2-(((2-hydroxyethyl)-amino)-methyl)-phenol |
| 0.01 g | 2,4-diamino-1-fluoro-5-methyl-benzenesulfate hydrate |
| 0.03 g | 1,3-dihydroxy-2-methylbenzene |
| 0.01 g | sodium hydroxide |
| 0.40 g | isopropyl alcohol |
| 7.60 g | ammonia (25% aqueous solution) |
| ad 100.00 g | water, desalinated |

The above hair dye composition (50 g) is mixed immediately before use with 50 g of hydrogen peroxide solution (6% aqueous solution) and the resulting mixture is applied onto the bleached hair. After a period of 30 minutes, the hair is rinsed with water, shampooed and dried. The hair is dyed an intensive brown shade.

Example 25
Hair Dye Composition including Direct Dyes

| | |
|---|---|
| 0.525 g | N-(2-methoxyethyl)-2-methyl-4-nitro-phenylamine |
| 0.380 g | 4-(di-(2-hydroxyethyl)-amino)-N-(2-hydroxyethyl)-2-nitroaniline |
| 0.358 g | 4-(ethyl-(2-hydroxyethyl)amino)-N-(2-hydroxyethyl)-2-nitroaniline |
| 0.0740 g | 4-(di(2-hydroxyethyl)amino)-2-nitroaniline hydrochloride |
| 10.000 g | isopropanol |
| 10.000 g | sodium salt of lauryl alcohol diglycol ether sulfate (28% aqueous solution) |
| ad 100.000 g | water |

The above exemplary dye composition is mixed immediately before use to form a ready-for-use dyeing agent. The pH is adjusted once with lactic acid (to an acidic pH of 5) and once with dilute ammonia solution (to an alkaline pH of 8). Bleached hair samples are then treated for 40 minutes at a temperature of 40° C. with respective portions of the dye composition, one acidic, the other basic. Subsequently, the hair is rinsed with water and dried. The hair, so treated, has a dark brown color.

Example 26
Hair Dye Composition including Direct Dyes

| | |
|---|---|
| 0.490 g | N-(2-methoxyethyl)-4-nitro-phenylamine |
| 0.709 g | 4-(ethyl-(2-hydroxyethyl)-amino)-N-(2-hydroxyethyl)-2-nitroaniline |
| 0.064 g | 5-chloro-4-((2,3-dihydroxypropyl)-amino)-2-nitroaniline |
| 0.088 g | 1-((4-aminophenyl)-azo)-2-hydroxy-7-(trimethylammonium)-naphthalene |
| 10.000 g | isopropanol |
| 10.000 g | sodium salt of lauryl alcohol diglycol ether sulfate (28% aqueous solution) |
| ad 100.000 g | water |

The pH was adjusted with a) lactic acid or b) dilute ammonia solution. Bleached hair, cotton or wool samples are treated for 40 minutes at a temperature of 40° C. with respective portions of the above-described dye composition, one acidic at a pH of 5 and one basic at a pH of 8. Subsequently, the fibers are rinsed with water and dried. The fibers, so treated, in each case have an intensive dark brown color.

Comparison Trials a) Checking the Washing-Out Behavior

The color values of 5 strands of dyed hair were determined. Subsequently, the strands of hair were shampooed five times consecutively for one minute with a neutral shampoo, then rinsed with water and dried. After this treatment, the color values of the individual strands were measured once again and the difference between the color values before and after the treatment was determined. The average of the results of 5 hair strands is given in Table 1.

b) Checking the Perspiration Resistance

The color values of 5 strands of dyed hair were determined. Subsequently, the strands of hair were immersed in a solution of synthetic perspiration, the composition of which is listed below

| | |
|---|---|
| 10.00 g | sodium chloride |
| 1.00 g | dipotassium phosphate |
| 0.25 g | DL-histidine |
| | lactic acid to a pH of 3.2 |
| 100.00 g | water | and left in the solution twice in each case for 24 hours at 37° C.

The hair strands were then rinsed with water and dried. After this treatment, the color values of the individual strands were measured once again and the difference between the color values before and after the treatment was determined. The average of the results of 5 strands of hair is given in Table 1.

c) Checking the Light-Fastness

The color values of 5 strands of dyed hair were determined. Subsequently, the strands of dyed hair were irradiated with an "Atlas Suntest CPS+" accelerated light equipment with a 1.5 kW xenon arc discharge lamp. The light fastness is evaluated by comparing the change in the color values measured with that of the standard depth of dyeing of the light fastness scale. After the treatment, the color values of the individual strands are measured once again and the difference between the color values before and after the treatment is determined. The average value of the results of 5 strands of hair is listed in Table 1.

The L*a*b* color values, given in the following Table, were measured with a Minolta type chromameter II color measuring equipment. The total color differences (αE color values measured) are given according to the CIE L*a*b color system. The "L" value represents the brightness (the lower the L value, the darker is the sample and conversely, the higher the L value, the brighter is the sample). The "a" value is a measure of the red portion or green portion (the greater or more positive the "a" value, the greater is the red portion and, conversely, the smaller or more negative the "a" value, the greater is the green portion). The "b" value is a measure of the blue portion and the yellow portion (the greater or more positive the "b" value, the greater is the yellow portion and, conversely, the smaller or more negative the "b" value, the greater is the blue portion). The ΔE value is a measure of the change in the color, the loss in intensity of the coloration being larger at larger values of ΔE.

TABLE 1

| Dyeing Agent of | Washing-out behavior ΔE value *) | Perspiration Resistance ΔE value *) | Light Fastness ΔE value *) |
|---|---|---|---|
| Example 1 | 26.7 | 35.0 | 42.7 |
| Example 2 | 16.2 | 31.2 | 38.8 |
| Comparison Trial: (Coloring agent of Example 1, in which the inventive N-(2-methoxyethyl)-4-nitro-phenylamine was replaced by a conventional dye [N-(2-hydroxyethyl)-4-nitrophenylamine], which is picked up directly) | 30.9 | 46.5 | 42.1 |

* averaged over 5 strands of hair

It is evident from the values above that, in comparison to conventional hair coloring agents, the inventive hair coloring agents (Examples 1 and 2) produce colorings, which are more resistant to washing out and to the effects of perspiration and light irradiation.

Unless stated otherwise, all percentages, given in the present application, are percentages by weight.

What is claimed is:

1. A dye composition for dyeing fibers, said dye composition having a pH of 3 to 12 and containing a solvent selected from the group consisting of water, alcohols, and mixtures thereof;

0.01 to 10 percent by weight of at least one dye compound of formula (I),

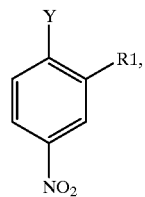

(I)

wherein R1 represents hydrogen or a methyl group and Y is an amino group of the formula —NHR2, R2 being either a cyclopropyl group, a methoxyethyl group or a methoxypropyl group; and from 0.5 to 30 percent by weight of a surfactant component selected from the group consisting of anionic surface-active substances, cationic surface-active substances, amphoteric surface-active substances, non-ionic surface-active substances, zwitterionic surface-active substances, and mixtures thereof.

2. A dye composition for dyeing fibers, said dye composition having a pH of 3 to 12 and containing a solvent selected from the group consisting of water, alcohols, and mixtures thereof;

0.01 to 10 percent by weight of a dye ingredient selected from the group consisting of N-(2-methoxyethyl)-4-nitrophenylamine, N-(2-methoxy-ethyl)-2-methyl-4-nitrophenylamine, 4-(4-nitrophenyl)-morpholine, N-(3-methoxy-propyl)-4-nitro-phenylamine, N-(3-methoxypropyl)-2-methyls-, nitrophenylamine, 4-(2-methyl-4-nitrophenyl)-morpholine, N-cyclopropyl-4-nitrophenylamine, 4-nitro-N-((tetrahydrofuran-2-yl)methyl)phenylamine, 2-methyl-4-nitro-N-(tetrahydrofuran-2-yl-methyl)-phenylamine, N-cyclopropyl-2-methyl-4-nitrophenylamine, and mixtures thereof; and from 0.5 to 30 percent by weight of a surfactant component selected from the group consisting of anionic surface-active substances, cationic surface-active substances, amphoteric surface-active substances, non-ionic surface-active substances, zwitterionic surface-active substances, and mixtures thereof.

3. The dye composition as defined in claim 1 or 2, further comprising from 0.1 to 10 percent by weight of a total amount of at least one developer substance and at least one coupler substance.

4. The dye composition as defined in claim 1 or 2, further comprising from 0.01 to 4 percent by weight of at least one direct-dyeing dye compound selected from the group consisting of nitro dyes, azo dyes, anthraquinone dyes and triphenylmethane dyes.

5. The dye composition as defined in claim 1 or 2, further comprising from 1 to 5 percent by weight of at least one polymer ingredient selected from the group consisting of unmodified polymers of natural origin, chemically modified polymers of natural origin and synthetic polymers.

6. A method of dyeing hair, said method comprising the steps of:

a) applying a hair dyeing composition to the hair in an amount sufficient for the dyeing of the hair;

b) allowing the hair dyeing composition applied to the hair in the applying step a) to act on the hair for a period of from 15 to 30 minutes; and then c) rinsing the hair with water and drying;

wherein said hair dyeing composition has a pH of from 3 to 12 and contains a solvent selected from the group consisting of water, alcohols, and mixtures thereof; 0.01 to 10 percent by weight of at least one dye compound of formula (I),

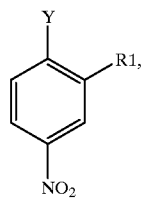

(I)

wherein R1 represents hydrogen or a methyl group and Y is an amino group of the formula —NHR2, R2 being either a cyclopropyl group, a methoxyethyl group or a methoxypropyl group; and from 0.5 to 30 percent by weight of a surfactant component selected from the group consisting of anionic surface-active substances, cationic surface-active substances, amphoteric surface-active substances, nonionic surface-active substances, zwitterionic surface-active substances, and mixtures thereof.

7. A method of dyeing hair, said method comprising the steps of:
a) mixing a hair dye composition with an oxidizing agent to form a hair dyeing mixture immediately prior to application to the hair;
b) applying the hair dyeing mixture to the hair in an amount sufficient for the dyeing of the hair;
c) allowing the hair dyeing mixture applied to the hair in the applying step b) to act on the hair for a time interval of from 15 to 45 minutes at 20° C. to 50° C.; and then
d) rinsing the hair with water and drying;
wherein said hair dyeing composition has a pH of from 2 to 5 and contains a solvent selected from the group consisting of water, alcohols, and mixtures thereof; from 0.1 to 10 percent by weight of at least one developer substance and at least one coupler substance; 0.01 to 10 percent by weight of at least one dye compound of formula (I),

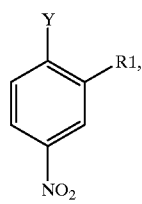

(I)

wherein R1 represents hydrogen or a methyl group and Y is an amino group of the formula —NHR2, R2 being either a cyclopropyl group, a methoxyethyl group or a methoxypropyl group; and from 0.5 to 30 percent by weight of a surfactant component selected from the group consisting of anionic surface-active substances, cationic surface-active substances, amphoteric surface-active substances, nonionic surface-active substances, zwitterionic surface-active substances, and mixtures thereof.

8. A method of dyeing hair, said method comprising the steps of:
a) applying a hair dyeing composition to the hair in an amount sufficient for the dyeing of the hair;
b) allowing the hair dyeing composition applied to the hair in the applying step a) to act on the hair for a period of from 15 to 30 minutes; and then
c) rinsing the hair with water and drying;
wherein said hair dyeing composition has a pH of from 3 to 12 and contains a solvent selected from the group consisting of water, alcohols and mixtures thereof;
0.01 to 10 percent by weight of a dye ingredient selected from the group consisting of N-(2-methoxyethyl)-4-nitrophenylamine, N-(2-methoxyethyl)-2-methyl-4-nitrophenylamine, 4-(4-nitrophenyl)-morpholine, N-(3-methoxypropyl)4-nitro-phenylamine, N-(3-methoxypropyl)-2-methyl-4-nitrophenylamine, 4-(2-methyl-4-nitrophenyl)-morpholine, N-cyclopropyl-4-nitrophenylamine, 4-nitro-N-((tetrahydrofuran-2-yl)methyl)phenylamine, 2-methyl-4-nitro-N-(tetrahydrofuran-2-yl-methyl)-phenylamine, N-cyclopropyl-2-methyl-4-nitrophenylamine, and mixtures thereof; and
from 0.5 to 30 percent by weight of a surfactant component selected from the group consisting of anionic surface-active substances, cationic surface-active substances, amphoteric surface-active substances, nonionic surface-active substances, zwitterionic surface-active substances, and mixtures thereof.

9. A method of dyeing hair, said method comprising the steps of:
a) mixing a hair dye composition with an oxidizing agent to form a hair dyeing mixture immediately prior to application to the hair;
b) applying the hair dyeing mixture to the hair in an amount sufficient for the dyeing of the hair;
c) allowing the hair dyeing mixture applied to the hair in the applying step b) to act on the hair for a period of from 15 to 45 minutes at 20° C. to 50° C.; and then
d) rinsing the hair with water and drying;
wherein said hair dyeing composition has a pH of from 3 to 12 and contains a solvent selected from the group consisting of water, alcohols, and mixtures thereof;
from 0.1 to 10 percent by weight of at least one developer substance and at least one coupler substance;
from 0.01 to 10 percent by weight of a dye ingredient selected from the group consisting of N-(2-methoxyethyl)-4-nitrophenylamine, N-(2-methoxyethyl)-2-methyl-4-nitrophenylamine, 4-(4-nitrophenyl)-morpholine, N-(3-methoxy-propyl)-4-nitrophenylamine, N-(3-methoxypropyl)-2-methyl-4-nitrophenylamine, 4-(2-methyl-4-nitrophenyl)-morpholine, N-cyclopropyl-4-nitrophenylamine, 4-nitro-N-((tetrahydrofuran-2-yl)methyl)phenylamine, 2-methyl-4-nitro-N-(tetrahydrofuran-2-yl-methyl)-phenylamine, N-cyclopropyl-2-methyl-4-nitrophenylamine, and mixtures thereof; and
from 0.5 to 30 percent by weight of a surfactant component selected from the group consisting of anionic surface-active substances, cationic surface-active substances, amphoteric surface-active substances, nonionic surface-active substances, zwitterionic surface-active substances, and mixtures thereof.

* * * * *